United States Patent [19]
Barker

[11] 4,075,886
[45] Feb. 28, 1978

[54] FRACTURE TOUGHNESS TEST METHOD
[75] Inventor: Lynn M. Barker, Salt Lake City, Utah
[73] Assignee: Reed Tool Company, Houston, Tex.
[21] Appl. No.: 789,318
[22] Filed: Apr. 20, 1977

Related U.S. Application Data

[63] Continuation of Ser. No. 718,994, Aug. 30, 1976, abandoned.

[51] Int. Cl.² .............................................. G01N 3/20
[52] U.S. Cl. ..................................... 73/88 R; 73/100
[58] Field of Search ........................ 73/100, 88 R, 101

[56] References Cited
U.S. PATENT DOCUMENTS
2,617,293  11/1952  Schnadt ................................ 73/100

FOREIGN PATENT DOCUMENTS
677,495  6/1939  Germany ............................. 73/88 R Primary Examiner—Anthony V. Ciarlante
Attorney, Agent, or Firm—Neal J. Mosely

[57] ABSTRACT

An improved method for testing fracture toughness of tungsten carbide, and more particularly sintered tungsten carbide, consists of preparing a specimen from a short rod of sample material by cutting thin longitudinal slots forming a V within the slotted portion of the sample. An initial crack is started at the tip of the V formed by the slots. After the initial crack is started, the specimen is loaded with a force perpendicular to the slot plane and the peak force required in advancing the crack is recorded. The peak force is linearly related to the critical stress intensity factor (fracture toughness) of the specimen material.

12 Claims, 8 Drawing Figures

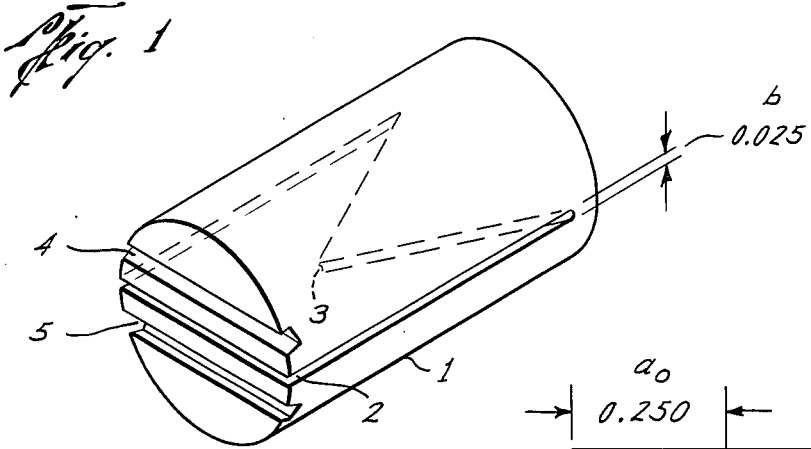
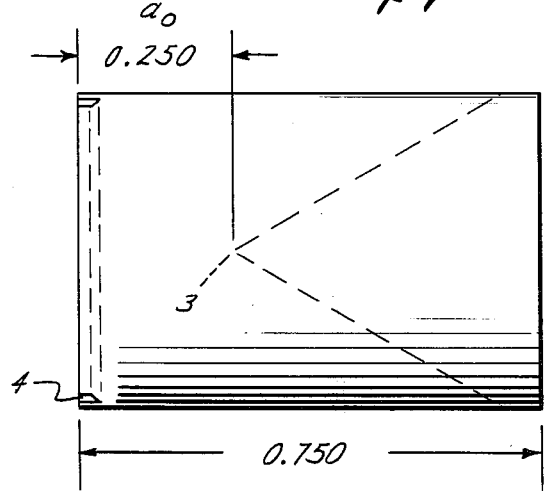
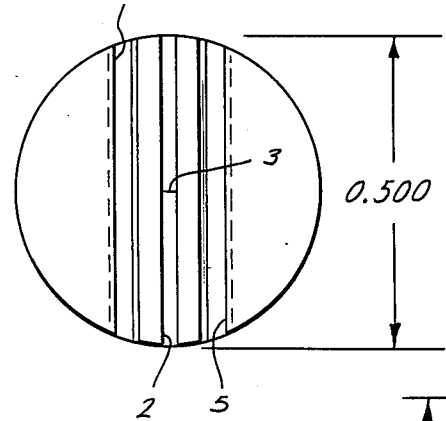
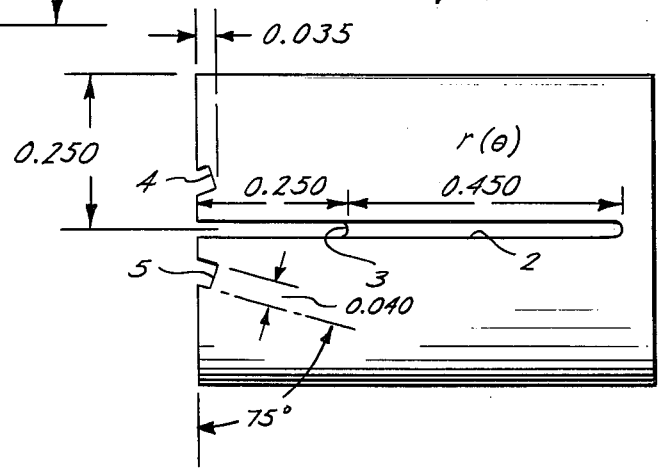

FRACTURE TOUGHNESS TEST METHOD

This application is a continuation of applicant's copending application Ser. No. 718,994, filed Aug. 30, 1976 now abandoned, for Fracture Toughness Test Method.

BACKGROUND OF THE INVENTION

1. Field of the Invention

This invention relates to new and useful improvements in methods for measuring fracture toughness of extremely hard and brittle materials such as tungsten carbide, and especially sintered tungsten carbide.

2. Discussion of the Prior Art

In the 1972 Ph.D. thesis by R. C. Lueth at Michigan State University there was reported a fracture toughness measurement procedure carried out on tungsten carbide. The Lueth procedure involved the use of long, slender specimens which are not readily available commercially. In the Lueth procedure a crack was introduced into a specimen and and the propagation of the crack arrested. Then the propagation of the crack further was measured and fracture toughness calculated. The main difficulty with the Lueth procedure was that the initial crack was hard to control and often ran most of the way through the sample.

In "FRACTURE TOUGHNESS OF CEMENTED TUNGSTEN CARBIDES" by Ingelstrom and Nordberg, Engineering Fracture Mechanics, Vol. 6, p. 597 (1974), another procedure is described for toughness testing. The authors used single-edge notched bend test specimens. A diamond indentation method of crack initiation was used. The same authors also used a compact tension specimen configuration in which they initiated the crack by an impact method and produced the required initial crack arrest by a strong lateral confining stress. The residual effect of the confining stress was shown to affect the measured fracture toughness if too large, yet did not produce the necessary crack arrest if too small.

An impact fracture toughness method is also described in Shockey and Curran U.S. Pat. No. 3,793,874. This procedure involves the formation of internal cracks in a specimen under repeated impacts and determination of crack size distribution. The change in crack distribution is used to calculate $a_c$, the critical crack half length of radius above which cracks grow and below which they do not grow.

SUMMARY OF THE INVENTION

It is therefore an object of this invention to provide a new and improved method for determining the fracture toughness of very brittle materials such as tungsten carbide, using small specimens.

Another object of this invention is to provide an improved method for evaluating differences in fracture toughness of highly brittle materials such as tungsten carbide.

Other objects will become apparent from time to time throughout the specification and claims as hereinafter related.

Briefly, this invention involves the preparation of small specimens by forming very thin intersecting slots in a V configuration. The material is cracked at the edge of the V and a small crack initiated and arrested. The portions of the test sample on opposite sides of the crack are then loaded and the force required for propagation of the crack measured. The peak force is linearly related to the critical stress intensity factor (fracture toughness) of the specimen material.

BRIEF DESCRIPTION OF THE DRAWINGS

FIG. 1 is an isometric view of a test specimen cut according to the method of this invention.

FIG. 2 is a plan view of the specimen shown in FIG. 1.

FIG. 3 is an end elevation of the specimen shown in FIG. 1.

FIG. 4 is a view in side elevation of the specimen shown in FIG. 1.

DESCRIPTION OF THE PREFERRED EMBODIMENT

Figure 5:
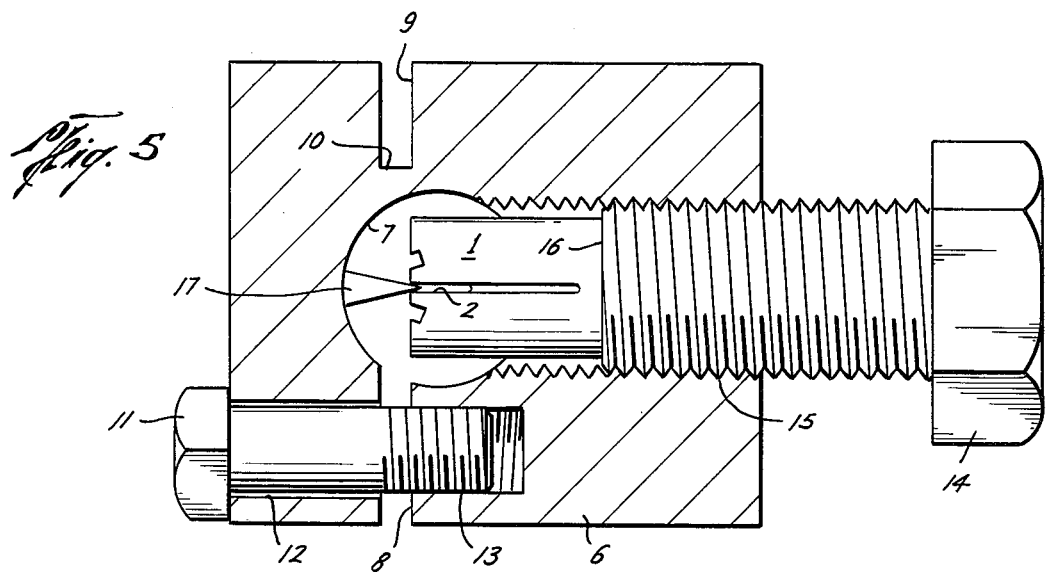
FIG. 5 is a view in longitudinal section showing an apparatus for initiating a crack in the specimen used in carrying out the test procedure of this invention.

The improved method of measuring fracture toughness in accordance with this invention involves first the preparation of a specimen from a short rod of sample material by cutting thin longitudinal slots as illustrated in FIG. 1. An initial crack is then started at the tip of the V formed by the slotting of the sample. The crack is arrested immediately after initiation. After the initial crack is started, the specimen is loaded with a force perpendicular to the plane of the slot such that the crack again begins to grow. The peak force required in advancing the crack through the specimen is recorded. The peak force is linearly related to the critical stress intensity factor (fracture toughness) of the specimen material.

The test method is divided into three phases:
1. Specimen preparation,
2. The test procedure, and
3. The interpretation of the data.

In order for the method to produce reliable results, all three phases must be carried out in such a way that no unacceptable errors are produced. In the more detailed discussion of each phase which follows it is assumed that the test result should represent the fracture toughness with an error of no more than a few percent. Therefore, the tolerances set forth are designed to keep the error from any one source to less than one percent.

The test method is primarily applicable to very hard, brittle materials such as tungsten carbide inserts of the type used in rock bits. The two most important properties for tungsten carbide inserts are wear resistance and toughness. From a practical point of view, the term wear resistance denotes the total property of resistance to wear made up of abrasion, impact and tearing. The term toughness applies to the ability to resist stresses tending to totally destroy (break) the insert.

Resistence to wear is measured by either the rate of erosion of a test piece pressed against a rotating abrasive surface or by a hardness test. Metals are classed as tough if fracture is preceded by large plastic deformation, and as brittle is fracture occurs without visible deformation. By this classification, all tungsten carbides would be designated as brittle. Nevertheless, designers of tungsten carbide inserts know that some grades of carbide are tougher than others. The test method of this invention has been developed to provide a means to measure the toughness of various grades of tungsten carbide, and particularly the cemented or sintered tungsten carbides.

In FIG. 1, there is shown a specimen blank 1 which is cylindrical in shape and slotted for testing. The blank is of a hard brittle material such as tungsten carbide, particularly a cemented or sintered tungsten carbide. Specimen blank 1 consists of a rod of 0.500 ± 0.002 inch diameter and 0.750 ± 0.005 inch long. The specimen 1 is slotted as at 2 for testing using a diamond saw blade 5.0 ± 0.2 inches in diameter. The blade is of a thickness sufficient to make a cut of 0.025 ± 0.005 inches width. The outside of the saw blade cut should be slightly rounded rather than flat. The slot 2 in specimen 1 is prepared in two cuts forming an internal V 3 within the slot. The slot dimensions are shown in FIGS. 2, 3 and 4. The slot plane should be centered in the sample to within ± 0.005 inch. The value of $a_o$ should be 0.250 ± 0.002 inch; however, the tolerance on $a_o$ can be relaxed to ± 0.015 inch if its actual value is measured and a correction factor is applied for the deviation from the 0.250 inch in the data interpretation phase of the experiment.

The internal V in slot 2 is expressed by the parameter $R(\theta)$. This parameter $R(\theta)$ is a measure of sharpness of the angle of the V. The larger the value of $R(\theta)$, the smaller the angle. $R(\theta)$ is defined as the projection of the edge of the V slot on the longitudinal axis of the specimen. In general, the projection of one side of the V will differ slightly from that of the other side. The two projections should agree to within 0.015 inch, and the $R(\theta)$ for the sample is taken as the average of the two values. The average $R(\theta)$ for the sample should be 0.450 ± 0.003 inch. However, the tolerance on $R(\theta)$ can be relaxed to ± 0.020 if its actual value is measured and a correction factor is applied in the date interpretation phase of the experiment for the deviation from 0.450 inch.

After the specimen is slotted, notches 4 and 5 are ground on the front face of the specimen to provide for the grips of the apparatus for applying a load force to the sample. Notches 4 and 5 are ground by a 0.040 ± 0.004 inch thich diamond wheel, as shown in FIG. 2. The depth of the notches is 0.035 ± 0.003 inch. They are ground at an angle of about 15° from the plane of the slots to keep the grips from slipping off the sample as force is applied.

Following the slotting and notching of the sample, a short pre-crack is started at the tip of the V. The pre-cracking is accomplished with a specially designed fixture, as shown in FIG. 5 for forcing a wedge of about 15° into the slot at the front of the specimen. The fixture is designed such that the elastic relaxation on initiation of the crack causes a minimum of uncontrolled wedge follow of the crack. This feature is necessary to keep the initial crack from propagating too far before it is arrested.

The fixture, generally designated 6, is shown in FIG. 5 and comprises a steel block having a center bore 7 and edge slots 8 and 9. The slot 8 extends into the edge of bore 7 while slot 9 extends only partially through and leaves a flexible hinge portion 10. The apparatus has a small screw 11 extending through a small bore 12 into a threaded bore 13. The fixture also includes a larger screw 14 extending through a threaded large bore 15. The large screw 14 has a flat end portion 16 on which the specimen 1 is supported. Wedge 17 is supported on the surface of bore 7 opposite specimen 1 and fits into the outer edge of crack 2 in specimen 1.

Figure 6:
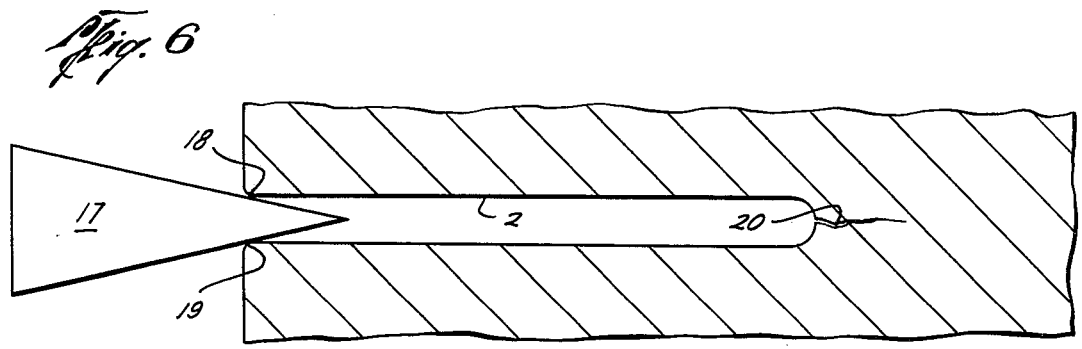
FIG. 6 is a detail view of the apparatus and specimen shown in FIG. 5 illustrating crack initiation.

The wedge 17 used in the experiments was made of steel. It was found that the sharp edge of the sawed slot 2 in the tungsten carbide samples tended to cut into the wedge as the wedge was forced into the slot. The sharp edges of the slot were therefore rounded slightly by using the edge of a diamond wheel as a file. The rounded edges 18 and 19 of slot 2 are shown in FIG. 6. In addition, a stopcock grease was used to lubricate the sliding surfaces.

After the sample and wedge surfaces were prepared, the sample was inserted in the fixture for crack initiation. With the sample and wedge in place, the large screw 14 was finger tightened onto the sample. The small screw 11 was then advanced until the solid hinge 10 was flexed by about one-fourth turn of the small screw 11. The small screw 11 was then backed off by one-fourth turn, and the large screw 14 was advanced again to a new finger tight position. The procedure was repeated until the crack was initiated. The initiation of the crack was accompanied by a distinct "tick" noise which should be listened for whenever the small screw 11 is being advanced.

In order to assure that the initial crack (shown at 20 in FIG. 6) did not propagate too far, its position in the sample was marked by dying its surface with India ink. This was done by allowing a drop of India ink to flow into the slot around the point of the V before the wedge was removed after pre-cracking. Surface tension draws the ink into the propped open crack.

Figure 7:
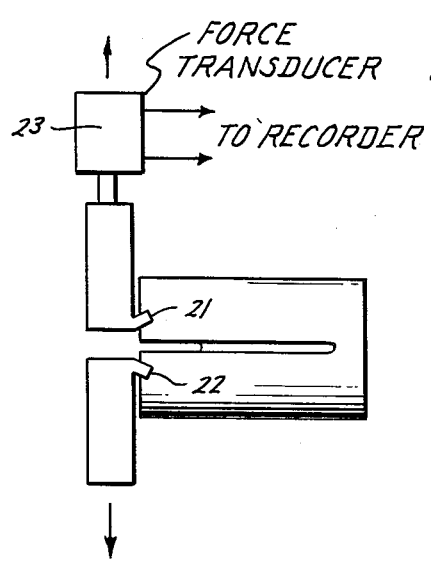
FIG. 7 is a schematic view illustrating the connection of the test specimen for recording force required for crack initiation and propagation.
Figure 8:
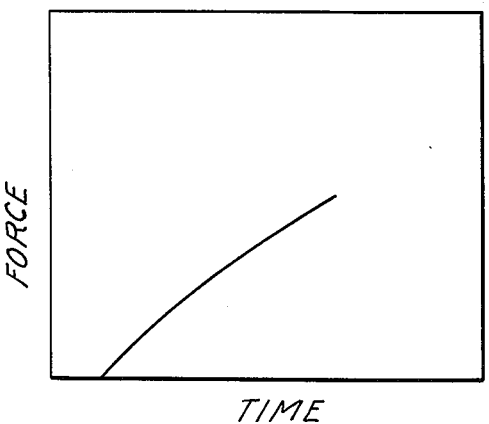
FIG. 8 is a view of a recorder illustrating the measurement of force against time for recording and calculating fracture toughness.

In carrying out the test, the specimen 1, with the small initial crack 20 formed therein, is tested on any machine capable of slowly increasing the force which loads the sample. Grips are fitted into the grooves on the front of the sample as illustrated at 21 and 22 in FIG. 7. The grips transmit the load to the sample. A force-measuring transducer 23 is placed in series with the sample and connected to a recorder shown schematically in FIG. 8 which plots force versus time during the test.

In order for the test to be valid, the initial crack which was dyed with India ink should be between 0.010 and 0.200 inch long. An initial crack which is shorter than 0.010 may not prevent another sudden cracking or "pop in" to beyond the 0.200 inch limit during the test. The maximum force (the desired raw data from the experiment) to propagate the crack occurs when the crack length is about 0.200 inch. Hence, an initial crack longer than 0.200 inch precludes measuring the peak force.

In addition to an acceptable initial crack, a valid test requires that the fracture must not leave the slotted guides before 0.200 inch from the point of the V. This requirement is again a consequence of the fact that the maximum force to propagate the crack occurs at about 0.200 inch, and the peak force is affected if the crack is not following the slot at that point. Put in quantitative terms, the tolerance of the slot-tracking by the crack at the 0.200 inch position is 0.002 inch on the width $b$ of the crack. The increase in $b$ due to imperfect tracking of the bottoms of the slots should not exceed 0.002 inch. However, an increase in crack width ($\Delta b$) of up to 0.020 inch is allowed if the deviation is measured and corrected for.

If the initial crack and the crack's tracking of the slots was acceptable, the data reduction can be started. The basic equation for the critical stress intensity factor, $K_{IC}$ (fracture toughness), is $$K_{IC} = K_{ICS} \frac{(F)}{(F_s)} \left[\frac{(1 - v_s^2)}{(1 - v^2)}\right]^{1/2} \quad (1)$$

where $K_{ICS}$ is the critical stress intensity factor of the material used as a standard, F is the maximum force applied to the sample during the test, $F_S$ is the maximum force applied during a similar test on a sample of the standard material, $v$ is Poisson's ratio, and $v_s$ is the Poisson's ratio of the standard material.

In evaluating the fracture toughness of tungsten carbide inserts, the relative values of the fracture toughness are important for rating various types of tungsten carbide, but the absolute value of $K_{IC}$ may not be important. Therefore, one reproducible grade of tungsten carbide can be used as a standard, and the fracture toughness of any other tungsten carbide can be rated against the standard. Let $K_r$ be the relative fracture toughness, and let $K_{rs}$, the relative fracture toughness of the standard material, be unity. In addition, note that the factor $[(1-v_s^2)/(1-v^2)]^{1/2}$ in Equation (1) can be taken as unity when comparing grades of tungsten carbide. Equation (1) then becomes $$K_r = F/F_s \quad (2)$$

In using Equation (2) to evaluate the relative fracture toughness, it is assumed that both F and $F_s$ were measured on samples whose dimensions fall within the tolerances specified in the section on Sample Preparation, and that the crack width was not appreciably affected by poor tracking of the slot guides. The most critical of these tolerances are the ± 0.002 inch for $a_o$, the ± 0.003 inch for $r(\theta)$ and the 0.002 inch for $\Delta b$ (the crack width change due to imperfect slot tracking).

One can correct for values of $a_o, r(\theta)$ and $\Delta b$ which are as much as 0.015, 0.020 and 0.020 inch, respectively, out of tolerance. The correction is made by using the actual values of $a_o, r(\theta)$ and $\Delta b$, measured in inches, in the equation $$F = CF' \quad (3)$$

where $$C = \frac{r(\theta)}{.45} (1 - 2.8\Delta b)[1 + 2.8(a_o - .25)]. \quad (4)$$

Here F' is the measured maximum force on the sample during the test, and F is the corrected value of F'. In Equation (4), the correction factor for $r(\theta)$, i.e., $r(\theta)/.45$, was derived from the assumption that F should vary in direct proportion to the crack width, b. A similar treatment was tried to correct for the change in b due to imperfect slot tracking by the crack. However, the resulting correction factor for $\Delta b$ was much too large. The corrections for $\Delta b$ and $a_o$ in Equation (4) are therefore empirical.

The results of 25 fracture toughness tests on the five different grades of tungsten carbide insert blanks are given in Table 1. The material of the first group of samples was used as the standard, and the five tested samples from this group are labeled S-1 through S-5. Six samples each of four additional grades of tungsten carbide were subsequently tested. Five tests of each grade were to be made, and a sixth sample was provided in case one was ruined in preparation for the test. The samples supplied by the manufacturer were all blanks; the slotting and grooving were done by the inventor.

The six samples of each grade supplied by the manufacturer were stamped with the grade number on the base of the sample. The samples in Table 1 are numbered with the grade number appearing first, and with the sample number of that grade appearing second. Thus, for example, sample 4-2 is the second sample of material number 4.

Sample 2-2 was ruined in preparation, and therefore does not appear in Table 1. Also, the pre-crack in sample 2-5 went to 0.29 inch, which is well beyond the 0.20 inch allowed, and therefore its F is invalid. Its data are included, however, because it provides an interesting point on the force versus crack length curve well beyond that of the peak force, which occurs at a crack length of about 0.20 inch. The peak force at 0.20 inch for material #2 is 216 pounds; sample 2-5 shows the force is down to 168 pounds at 0.29 inch.

TABLE 1

| Sample Number | $a_o$ (in) | $r(\theta)$ (in) | $\Delta b$ (in) | F' (lb) | C | F (lb) |
|---|---|---|---|---|---|---|
| S-1 | .263 | .450 | 0 | 186 | 1.036 | 193 |
| S-2 | .251 | .488[a] | 0 | 187 | 1.087 | 203[b] |
| S-3 | .249 | .441 | .016 | 207 | .933 | 193 |
| S-4 | .252 | .440 | 0 | 200 | .983 | 197 |
| S-5 | .251 | .440 | 0 | 201 | .981 | 197 |
| 1-1 | .244 | .451 | .010 | 190 | .958 | 182 |
| 1-2 | .243 | .454 | 0 | 180 | .989 | 178 |
| 1-3 | .240 | .457 | 0 | 184 | .987 | 182 |
| 1-4 | .244 | .453 | .008 | 192 | .968 | 186 |
| 1-5 | .241 | .453 | 0 | 180 | .981 | 177 |
| 2-1 | .258 | .454 | 1.008 | 215 | 1.008 | 217 |
| 2-3 | .242 | .458 | 0 | 223 | .995 | 222 |
| 2-4 | .247 | .457 | .014 | 223 | .968 | 216 |
| 2-5 | .248 | .464 | 0 | 164[c] | 1.025 | 168[c] |
| 2-6 | .260 | .446 | 0 | 206 | 1.019 | 210 |
| 3-1 | .249 | .452 | .002 | 211 | .992 | 209 |
| 3-2 | .252 | .459 | 0 | 206 | 1.026 | 211 |
| 3-3 | .269[a] | .443 | 0 | 205 | 1.037 | 213[b] |
| 3-4 | .247 | .452 | 0 | 202 | .996 | 201 |
| 3-5 | .258 | .448 | .009 | 207 | .992 | 205 |
| 4-1 | .252 | .451 | .003 | 205 | 1.016 | 208 |
| 4-2 | .238 | .463 | 0 | 212 | .994 | 211 |
| 4-3 | .258 | .453 | .018 | 212 | .977 | 207 |
| 4-4 | .259 | .457 | .006 | 197 | 1.008 | 199 |
| 4-5 | .247 | .454 | .010 | 212 | .972 | 206 |

[a] Out of tolerance.
[b] Questionable data; tolerances not met.
[c] Data invalid; pre-crack was too long.

The test data shown in Table 1 are summarized in Table 2 where the best values of F and the relative fracture toughness are given. The difference between materials 3 and 4 is probably not significant; however, the other differences are significant and could be reproduced in subsequent tests. The total spread of the valid data for each material is ± 3 percent or less; thus the average relative fracture toughness values in Table 2 are accurate to ± 2 percent or better.

TABLE 2

| | Summary of Fracture Toughness Test Results | |
|---|---|---|
| Material | F (lb) | $K_r$ (Rel. Frac. Toughness) |
| Standard | 196 | 1.00 ± .02 |
| 1 | 181 | .92 ± .02 |
| 2 | 216 | 1.10 ± .02 |
| 3 | 208 | 1.06 ± .02 |
| 4 | 206 | 1.05 ± .02 |

The fracture toughness test described above has been used for testing cemented or sintered tungsten carbide samples and has been shown to perform well. The test used samples which are roughly the same size and shape as inserts used in drill bits so that the samples have the same properties as drill bit inserts. The machining tolerances used were as small as ± 0.002 inch, but correction factors for the data have been generated which allow the machining tolerances to be relaxed. With reasonable care, using the relaxed tolerances and correction factors, the test method can easily distinguish between materials whose fracture toughness differ by 3 percent or more.

In the sample preparation and test procedure described above, the dimensions and tolerances given are for a test specimen corresponding in size to a 0.500 inch diameter tungsten carbide drill bit insert. The dimensions would obviously be scaled up or down for larger or smaller test specimens. The dimensions and tolerances for any particular test specimen are somewhat critical if an acceptably low test error is to be obtained.

I claim:

1. A method of measuring the fracture toughness of hard brittle materials comprising
   forming a short rod-shaped test specimen,
   cutting slots in said specimen in a single plane intersecting to form a single slot having an internal V shape,
   applying an opening force at the open end of said single slot to form an initial short crack at the apex of said V,
   applying slowly increasing forces to the slotted end of said specimen perpendicular to said slot in opposite directions tending to open said slot and propagate said crack, and
   measuring the peak force applied in propagating said crack prior to breaking said specimen,
   said peak force being linearly related to the fracture toughness of the specimen.

2. A method according to claim 1 in which said hard brittle material comprises tungsten carbide.

3. A method according to claim 1 of measuring the relative fracture toughness of hard brittle materials in which the measured peak force is related to the measured peak force applied in propagating a crack in and breaking the standard test specimen to establish the relative fracture toughness thereof.

4. A method according to claim 3 in which said initial opening force is applied by a wedge.

5. A method according to claim 4 in which said initial opening force is applied to the specimen in a fixture having a threaded adjustable support for the specimen, and a threaded force applicator for said wedge.

6. A method according to claim 4 in which the length of the initial crack is measured by staining.

7. A method according to claim 3 in which the length of the initial crack is less than the crack length at the point of application of peak force in crack propagation.

8. A method according to claim 3 in which the crack propagation forces are applied by a tensile test machine connected to a transducer and recorder for recording force vs. time.

9. A method according to claim 3 in which the relative fracture toughness is calculated by application of the formula $$K_r = F/F_s$$

where $K_r$ is the relative fracture toughness, $F$ is the peak force applied in the test, and $F_s$ is the peak force applied to a standard test specimen.

10. A method according to claim 3 in which said hard brittle material comprises tungsten carbide.

11. A method according to claim 10 in which the test specimen is a rod 0.500 ± 0.002 inch in diameter and 0.750 ± 0.005 inch in length, the slot has dimensions $a_o$ = 0.250 ± 0.002 inch and $r(\theta)$ = 0.450 ± 0.003 inch.

12. A method according to claim 10 in which the initial opening force is applied by a wedge and the edges of the slot into to which the wedge is applied are rounded.

* * * * *